(12) United States Patent
Poirier et al.

(10) Patent No.: US 8,093,441 B2
(45) Date of Patent: Jan. 10, 2012

(54) REMOVAL OF LIGHT FLUOROALKANES FROM HYDROCARBON STREAMS

(75) Inventors: Marc-André Poirier, Sarnia (CA); Robert J. Falkiner, Mississauga (CA)

(73) Assignee: ExxonMobil Research and Engineering Company, Annandale, NJ (US)

( * ) Notice: Subject to any disclaimer, the term of this patent is extended or adjusted under 35 U.S.C. 154(b) by 266 days.

(21) Appl. No.: 12/590,419

(22) Filed: Nov. 6, 2009

(65) Prior Publication Data

US 2010/0160706 A1 Jun. 24, 2010

Related U.S. Application Data

(60) Provisional application No. 61/203,050, filed on Dec. 18, 2008.

(51) Int. Cl.
*C07C 7/12* (2006.01)
(52) U.S. Cl. ............... 585/820; 585/733; 208/262.1
(58) Field of Classification Search .................. None
See application file for complete search history.

(56) References Cited

U.S. PATENT DOCUMENTS

| | | | |
|---|---|---|---|
| 2,347,945 A | 5/1944 | Frey | |
| 2,403,714 A | 7/1946 | Frey | |
| 3,624,166 A | 11/1971 | Fuhrmann et al. | |
| 4,317,949 A | 3/1982 | Vaughan | |
| 4,820,884 A | 4/1989 | Weigert | |
| 5,396,022 A | 3/1995 | Wu et al. | |
| 7,074,434 B2 | 7/2006 | Lambert et al. | |

FOREIGN PATENT DOCUMENTS

EP  0 924 287 A2  6/1999

OTHER PUBLICATIONS

Gokul Chandra, M. M. Sharma; Catalysis Letters 1993, Received: Mar. 20, 1992, Accepted Apr. 19, 1993, Abstract.
Kozo Tanabe, Wolfgang F. Holderich, "Industrial application of solid acid-base catalysts," Applied Catalysis A: General, vol. 181, Issue 2, May 1999, pp. 399-434, Abstract.
Brian R. Greally, Graham Nickless, Peter G. Simmonds, "Retention behavaiour of volatile C1-C3 fluoroalkanes upon selected preconcentration adsorbents," Journal of Chromatography A, 1133 (2006) pp. 49-57.

*Primary Examiner* — Tam M Nguyen

(57) ABSTRACT

The removal of fluoroalkanes from fluoroalkane-containing hydrocarbon streams, preferably $C_3$ to $C_5$ hydrocarbon streams. The fluoroalkane-containing hydrocarbon stream is contacted with an adsorbent containing a strong acid function, preferably a silica gel or a strong cation ion-exchange resin having sulfonic acid functionality.

19 Claims, No Drawings

REMOVAL OF LIGHT FLUOROALKANES FROM HYDROCARBON STREAMS

This application claims the benefit of U.S. Provisional Application No. 61/203,050 filed Dec. 18, 2008.

FIELD OF THE INVENTION

The present invention relates to the removal of fluoroalkanes from fluoroalkane-containing hydrocarbon streams, preferably $C_3$ to $C_5$ hydrocarbon streams. The fluoroalkane-containing hydrocarbon stream is contacted with an adsorbent containing a strong acid function, preferably a silica gel or a strong cation ion-exchange resin having sulfonic acid functionality.

BACKGROUND OF THE INVENTION

Certain processes for upgrading hydrocarbon feeds using fluorine-containing catalysts generate organic fluorine-containing by-products. These processes may involve reactions such as polymerization and alkylation of relatively low boiling hydrocarbons to produce octane enhancers. The fluorine-containing by-products, which are typically fluoroalkanes, are undesirable because they can decompose at elevated temperatures, for example during fractional distillation or combustion, to form hydrofluoric acid (HF) which is corrosive and toxic. One process of particular interest is the HF alkylation of relatively low-boiling hydrocarbons using hydrofluoric acid to produce higher boiling hydrocarbons used as octane enhancers. Although the precise compositions of the fluoroalkanes are difficult to establish, it is believed they are predominately $C_4$ fluoroalkanes, more particularly 2-fluoro-2-methylpropane (tert-butyl) fluoride. The presence of these light fluoroalkanes in n-butane and other hydrocarbon streams is undesirable and may limit the applicability of liquid petroleum gas (LPG) for some purposes, or result in lower market value.

Various attempts have been made to remove undesirable fluoroalkanes from hydrocarbon streams. For example, U.S. Pat. No. 5,396,022, which is incorporated herein by reference, relates to the defluorination of alkane streams comprising treating an alkane/fluoroalkane stream with an acidic alumina, preferably a sulfur-containing alumina, to reduce the amount of fluoroalkanes in the feed.

Also, U.S. Pat. Nos. 2,347,945 and 2,403,714, both of which are incorporated herein by reference, relate to the removal of organic fluorine compounds from a hydrocarbon stream by contacting the hydrocarbon stream with porous materials, such as alumina gel, activated alumina, dehydrated bauxite, chromium oxide, a mixture of alumina and chromium oxide, metals of the iron group, and the like.

While commercially viable processes exist for removing fluoroalkanes from light hydrocarbon streams, there nevertheless remains a need in the art for ever more efficient and cost effective processes for removing these fluoroalkanes.

SUMMARY OF THE INVENTION

In accordance with the present invention there is provided a process for removing fluoroalkanes from hydrocarbon streams comprised of $C_2$ to $C_{10}$ hydrocarbons and containing from about 0.05 to about 1 wt. % $C_3$ to $C_5$ fluoroalkanes, wherein the process comprises contacting the fluoroalkane-containing hydrocarbon stream with an adsorbent having strong acid functionality, which contacting is performed at a temperature from about −40° C. to about 60° C.

In a preferred embodiment the fluoroalkane-containing hydrocarbon stream is comprised of at least 75 wt. % $C_3$ to $C_5$ hydrocarbons.

In another preferred embodiment the acid functionality of the adsorbent is sulfonic acid.

In still another preferred embodiment the adsorbent is a silica gel containing a sulfonic acid functionality.

In yet another preferred embodiment the fluoroalkanes to be removed are characterized as having from about 3 to 5 carbon atoms and 1 or 2 fluorine atoms.

In other preferred embodiments the fluoroalkanes to be removed are selected from the group consisting of 1-fluoropropane, 2-fluoropropane, 2-fluoro-2-methylpropane, 1-fluorobutane, 2-fluorobutane, 1-fluoro-2-methylbutane, 1-fluoropentane, 2-fluoropentane, 2,2-difluorobutane, 3-fluoropentane, 1,2-difluoropentane, 1-fluoro-3-methylbutane, and mixtures thereof.

DETAILED DESCRIPTION OF THE INVENTION

Hydrocarbon streams on which the present invention can be practiced are those relatively low boiling streams containing from about 0.05 to about 1 wt. %, preferably from about 0.1 to about 0.5 wt. % fluoroalkanes based on the total weight of the hydrocarbon stream. These hydrocarbon streams are typically referred to as $C_2$ to $C_{10}$, preferably $C_3$ to $C_5$ hydrocarbon streams. That is, these fluoroalkane-containing hydrocarbon streams are predominantly comprised of hydrocarbons having from about 2 to about 10, preferably from about 3 to 5 carbon atoms. In preferred embodiments of the present invention fluoroalkane-containing hydrocarbon stream contains at least 75 wt % $C_3$ to $C_5$ hydrocarbons, and even more preferably at least 90 wt % $C_3$ to $C_5$ hydrocarbons, based on the dry weight (water-free) of the fluoroalkane-containing hydrocarbon stream.

The fluoroalkanes targeted for removal by the present invention are typically present in low-boiling point hydrocarbon streams such as propane, n-butane, isobutene, pentane, and isopentane produced from an alkylation process. Fluoroalkanes can also be present in a hydrocarbon streams from depropanization or debutanization processes. The predominant fluoroalkane-containing hydrocarbon stream is typically a hydrocarbon stream containing $C_3$ to $C_5$ hydrocarbons that results from an hydrofluoric (HF) alkylation process wherein an isoparaffin, such as isobutane, is reacted with one or more olefins, such as butylene, to produce a higher molecular weight branched chain paraffin (i.e., "alkylate"). Branched chain paraffins are commercially important for increasing the octane of the gasoline pool and for their sensitivity to octane-enhancing additives. The HF alkylation process is typically conducted at temperatures from about 10° C. to about 100° C. and at an effective pressure to maintain a liquid phase in the alkylation reaction zone. This effective pressure will typically range from about 20 to about 1200 psig, preferably from about 50 to about 500 psig. Olefin feed rates in the alkylation process can vary from 0.01 to 10 weight hourly space velocity (WHSV), preferably from about 0.05 to about 5 WHSV. Contact times for isoparaffin:olefin feed with the alkylation catalyst will typically range from about 0.1 second to about 100 minutes, preferably from about 10 seconds to about 20 minutes.

The resulting stream from HF alkylation is typically treated over a potassium hydroxide bed to remove water and at least a fraction of preferably substantially all of, residual hydrofluoric acid. However, a significant problem existing in the industry, is that this treatment does not remove fluoroalkane impurities. The present invention is directed to removing these fluoroalkane impurities from such light hydrocarbon product streams. It is not uncommon for petroleum refineries to produce n-butane streams containing up to about 0.6 wt % fluoride ions that, because of the high fluoride content, must be sold at a reduced market price.

It has unexpectedly been found by the inventors of the present invention hereof that contacting a $C_2$ to $C_{10}$, preferably $C_3$ to $C_5$ paraffinic stream containing a low level, such as about 0.46 wt % of an alkyl fluoride, such as tert-butyl fluoride, with a small amount of adsorbent of the present invention, such as silica gel having sulfonic acid functionality, at an effective temperature, will remove substantially all of the tert-butyl fluoride. The silica gel is preferably functionalized with sulfonic acid groups by treating or reacting the silica gel with chlorosulfonic acid. Commercial alumina adsorbents designed to remove alkyl fluorides and HF from hydrocarbons streams using a "sulfur containing alumina" as taught in U.S. Pat. No. 5,396,022 do not significantly remove tert-butyl fluoride under the same testing conditions.

In accordance with a preferred embodiment of this invention, the method for removing fluoroalkane contaminants from the hydrocarbon stream comprises contacting the fluoroalkane-containing hydrocarbon feed stream with an effective amount of an adsorbent having strong acid functionality at a temperature in the range from −40° C. to 60° C. to remove at least about 90 wt % of the fluoroalkanes, preferably to remove more than about 95 wt % of the fluoroalkanes, based on the dry weight of the hydrocarbon feed.

Any suitable adsorbent containing strong acid groups, preferably sulfonic acid groups can be used in the practice of the present invention. Both mineral based materials having Si atoms to which the acid group can bond, and organic based materials, preferably polymeric materials having carbon atoms to which the strong acid group can bond, can be used in the practice of the present invention. Non-limiting examples of suitable mineral materials include silica gels and both naturally occurring and synthetic zeolites and clays. The preferred mineral materials for the present invention are the silica gels. Non-limiting examples of suitable organic materials include strong cation exchange resins, preferably the styrene:divinyl benzene copolymers functionalized with sulfonic acid groups. Styrene:divinyl benzene copolymer strong cation exchange resins are commercially available from various vendors, such as the resins marketed under the tradename Amberlyst® from Rohm and Hass or from Sigma-Aldrich. The ion-exchange resins used in the practice of the present invention can be used in either the gellular or macroreticular spherical bead form.

As previously mentioned, the fluoroalkanes that can be present as impurities in the hydrocarbon (alkane)/fluoroalkane feed stream of the present invention will typically be fluoroalkanes containing about 3 to 5 carbon atoms and one or two fluorine atoms. Non-limiting examples of such fluoroalkanes include 1-fluoropropane, 2-fluoropropane, 2-fluoro-2-methylpropane, 1-fluorobutane, 2-fluorobutane, 1-fluoro-2-methylbutane, 1-fluoropentane, 2-fluoropentane, 2,2-difluorobutane, 3-fluoropentane, 1,2-difluoropentane, 1-fluoro-3-methylbutane and a mixture thereof. The fluoroalkanes targeted by the processes of the present invention are preferably the monofluoroalkanes, more preferably 2-fluoro-2-methylpropane.

The contacting of the hydrocarbon/fluoroalkane feed with the functionalized adsorbent of the present invention can be carried out in any suitable manner including both a batch process or a continuous fixed bed process. A continuous fixed bed process is preferred. The instant process can be carried out at temperatures in the range from about −40° C. to about 60° C., preferably from about −20° C. to about 40° C. which is more typical of conditions for LPG production, storage, and handling systems. The hydrocarbon product obtained from the practice of the present invention will preferably contain less than about 0.001 wt % of fluoroalkanes and a negligible amount of hydrofluoric acid, preferably after further treatment, such as being passed through a KOH bed or other suitable absorbent for the hydrofluoric acid produced in the process.

EXAMPLES

The present invention is illustrated in greater detail by the specific examples presented below. It is understood that these examples are illustrative embodiments and are not intended to be limiting in any way.

Example 1

Pyridinium Polyhydrogen Fluoride

A 250 mL polyolefin bottle was equipped with a polyolefin gas-inlet and drying tube inserted through the holes in the cap and sealed with Teflon tape. The bottle was charged with 37.5 g (0.475 mole) of pyridine and cooled in an acetone-dry ice bath. After the pyridine solidified, 87.5 g (4.37 mole) of anhydrous hydrogen fluoride was condensed from a cylinder into the bottle through the inlet tube. The amount of hydrogen fluoride was determined by weighing the bottle. After the hydrogen fluoride has cooled, the bottle was cautiously swirled with cooling until the solid dissolved. The solution was then safely allowed to warm to room temperature.

Tert-Butyl Fluoride

A 500 mL polyolefin bottle was equipped with a Teflon-coated magnetic stirring bar and a polyolefin drying tube inserted through a hole in the cap and sealed with Teflon tape. The bottle was charged with 4.88 g (0.066 mole) of tert-butanol and 100 mL of pyridinium polyhydrogen fluoride. The solution was allowed to stir for 5 hours at 0° C., after which 250 mL of petroleum ether was added, and stirring continued at 0° C. for another 15 minutes. A two-phase system resulted and was transferred to a 500 mL polyolefin separatory funnel, and the bottom layer was discarded. One of the phases was an organic layer that was washed successively with 100 mL of water, 100 mL of saturated sodium hydrogen carbonate solution and again with 100 mL water, then dried over anhydrous magnesium sulfate. The temperature was maintained at about 0° C. The organic layer was filtered, and the tert-butyl fluoride was allowed to distill, yielding 2.8 g (55%) of a clear liquid boiling at 12° C.

Preparation of the Tert-Butyl Fluoride/n-Pentane Stock Solution 500 mL of cold n-pentane kept at 0° C. was poured in a glass graduated cylinder. To the n-pentane was added 2.3 mL of tert-butyl fluoride also kept at 0° C. The resulting solution was thoroughly mixed and analyzed by CAP-GC by the CGSB method for gasoline. The concentration of the tert-butyl fluoride was found to be 0.43 wt %. The solution was kept in the refrigerator at 0° C.

Example 2

This example describes the various adsorbents tested in the following examples:

Activated Alumina, 28×48 mesh, provided by the BASF Company, The Woodlands, Tex. under the product designation DD-6.

Activated Alumina, 28×48 mesh, provided by the BASF Company, The Woodlands, Tex. under the product designation CPN.

Activated Alumina, 7×14 mesh, provided by the BASF Company, The Woodlands, Tex. under the product designation HF-200.

Activated Alumina, 7×14 mesh, provided by the BASF Company, The Woodlands, Tex. under the designation HF-200 XP.

Davisil® Silica gel, Grade 646 obtained from Grace Davison.

Amberlyst® 15 ion exchange resin obtained from Sigma-Aldrich, Cat. # 216380-25G.

Dynasorb® 200 Attapalgite Clay, 24×48 mesh obtained from Dynamic Catalysts and Adsorbents Inc.

Spent MHIS catalyst characterized by the following elemental composition: 38.3 wt % Al, 0.5 wt % Si, 6.8 wt % Co, 29.9 wt % Mo, 19.3 wt % O, and 5.7 wt % S.

Spent RT-601 catalyst (hydrotreating catalyst) characterized by the following elemental composition: 6.1 wt % C, 1.4 wt % H, 8.2 wt % O, 36.1 wt % Al, 2.1 wt % Si, 9.3 wt % S, 6.0 wt % Co and 30.8 wt % Mo.

Spent FCC (fluid catalytic cracking) alumino-silicate catalyst characterized by the following elemental composition: 41.7 wt % Al, 32.3 wt % Si, 5.7 wt % S and 20.3 wt % O.

Spent MHIS D-116B catalyst characterized by the following elemental composition: 7.0 wt % C, 1.5 wt % H, 8.1 wt % O, 38.8 wt % Al, 1.5 wt % Si, 7.5 wt % S, 7.7 wt % Ni and 27.9 wt % Mo.

Preparation of the Sulfonated Silica Gel

The sulfonated silica gel adsorbent was prepared by stirring at ambient temperature (25° C.) 150 g Davisil® grade 646 silica gel with 400 mL chloroform and 50 mL chlorosulfonic acid. The slurry was filtered, dried with a stream of nitrogen, and used without further treatment.

Preparation of the Attapalgite Clay Treated with Ammonium Sulfate

The sulfur loaded Attapalgite Clay was prepared by stirring at ambient temperature in a 250 mL glass beaker 20 g of Dynasorb® Attapalgite Clay with 1.3 g ammonium sulfate dissolved in 100 mL distilled water. The slurry was then filtered and dried at 100° C. for 3 hours.

Example 3

This example illustrates the effectiveness of sulfonated silica gel of this invention for removing tert-butyl fluoride at ambient temperature conditions. A 10% potassium hydroxide solution in methanol was ineffective for removing the tert-butyl fluoride. The process utilizing an untreated silica gel resulted in a modest removal of 21.7% of the tert-butyl fluoride whereas the process of the present invention utilizing a sulfonated silica gel gave an outstanding 100% removal of the tert-butyl fluoride present in the hydrocarbon sample.

Procedure 20 mL of stock solution C was placed in a 50 L crimped glass GC bottle with the material to be tested. The bottle was placed on a Lab-Line® Orbit Shaker and shook for 20 hours at 30° C. After that period, the n-pentane portion was analyzed by CAP-GC. The tert-butyl fluoride retention time was 9.97 minutes.

The results of the various tests are shown in Table 1.

TABLE 1

| Test # | Description | TBF, wt % 20 hours | % Removal |
|---|---|---|---|
| 1 | Stock TBF in n-pentane (0.43 wt %) Blank | 0.432 | 0 |
| 2 | 5 mL Aqueous KOH 10 wt % | 0.434 | 0 |
| 3 | 10 mL Methanolic KOH 10 wt % | 0.419 | 2.9 |
| 4 | 10 mL Methanolic KOH 10% with 10 wt % H2O | 0.418 | 3.1 |
| 5 | 0.10 g HF-200 | 0.414 | 4.0 |
| 6 | 0.10 g DD-6 | 0.420 | 2.7 |
| 7 | 0.10 g HF-200XP | 0.433 | 0 |
| 8 | 0.10 g CPN | 0.424 | 1.7 |
| 9 | 0.30 g HP-200 | 0.414 | 4.0 |
| 10 | 0.30 g Spent MHIS regen. Catalyst | 0.397 | 8.0 |
| 11 | 0.30 g Silica Gel | 0.338 | 21.7 |
| 12 | 0.30 g Attapalgite Clay/(NH4)SO4 | 0.421 | 2.5 |
| 13 | 0.30 g Spent RT-601 Catalyst | 0.383 | 11.2 |
| 14 | 0.30 g Spent FCC Catalyst | 0.344 | 20.3 |
| 15 | 0.30 g MHIS D-116B Catalyst | 0.416 | 3.6 |
| 16 | 0.30 g sulfonated Silica Gel | 0 | 100 |
| 17 | 0.10 g sulfonated Silica Gel | 0 | 100 |
| 18 | 0.30 g Amberlyst ® 15 ion exchange resin | 0.010 | 97.8 |
| 19 | 0.10 g Amberlyst ® 15 ion exchange resin | 0.010 | 97.8 |

What is claimed is:

1. A process for removing fluoroalkanes from a fluoroalkane-containing hydrocarbon stream comprised of $C_2$ to $C_{10}$ hydrocarbons and from about 0.05 to about 1 wt. % $C_3$ to $C_5$ fluoroalkanes, which process comprises contacting said fluoroalkane-containing hydrocarbon stream with an adsorbent having strong acid functionality at a temperature from about −40° C. to about 60° C. wherein the absorbent is a mineral based adsorbent selected from the group consisting of zeolite, silica gels, and a polymeric strong cation resin.

2. The process of claim 1, further comprising producing a hydrocarbon product stream having a fluoroalkane content by wt % that is less than 10% of the fluoroalkane content by wt. % of the fluoroalkane-containing hydrocarbon stream.

3. The process of claim 1, wherein the fluoroalkane-containing hydrocarbon stream is comprised of at least 75 wt. % $C_3$ to $C_5$ hydrocarbons.

4. The process of claim 1, wherein fluoroalkanes to be removed are characterized as having from about 3 to 5 carbon atoms and 1 or 2 fluorine atoms.

5. The process of claim 1, wherein the acid functionality of the adsorbent is sulfonic acid.

6. The process of claim 1, wherein the adsorbent is selected from the group consisting of mineral based adsorbents and organic based adsorbents.

7. The process of claim 1, wherein the adsorbent is comprised of a silica gel with a sulfonic acid functionality.

8. The process of claim 1, wherein the adsorbent is comprised of a polymeric strong cation resin.

9. The process of claim 8, wherein the polymer strong cation exchange resin is a styrene/divinyl benzene copolymer resin having a sulfonic acid functionality.

10. The process of claim 4, wherein the fluoroalkanes are selected from the group consisting of 1-fluoropropane, 2-fluoropropane, 2-fluoro-2-methylpropane, 1-fluorobutane, 2-fluorobutane, 1-fluoro-2-methylbutane, 1-fluoropentane, 2-fluoropentane, 2,2-difluorobutane, 3-fluoropentane, 1,2-difluoropentane, 1-fluoro-3-methylbutane, and mixtures thereof.

11. The process of claim 1, wherein the fluoroalkanes content in the hydrocarbon feed is from about 0.01 wt. % to about 0.5 wt. % based on the total weight of hydrocarbon feed.

12. The process of claim 2, wherein the fluoroalkanes content in the hydrocarbon feed is from about 0.01 wt. % to about 0.5 wt. % based on the total weight of hydrocarbon feed.

13. The process of claim 12, wherein the fluoroalkane-containing hydrocarbon stream is comprised of at least 75 wt. % $C_3$ to $C_5$ hydrocarbons.

14. A process for removing fluoroalkanes from a fluoroalkane-containing hydrocarbon stream comprised of $C_3$ to $C_5$ hydrocarbons and containing from about 0.01 to about 0.5 wt. % $C_3$ to $C_5$ fluoroalkanes, which process comprises contacting said fluoroalkane-containing hydrocarbon stream with an adsorbent having strong acid functionality at a temperature from about −20° C. to about 40° C. wherein the adsorbent is selected from the group consisting of silica gel polymeric strong cation exchange resins.

15. The process of claim 14, further comprising producing a hydrocarbon product stream having a fluoroalkane content by wt % that is less than 10% of the fluoroalkane content by wt % of the fluoroalkane-containing hydrocarbon stream.

16. The process of claim 14, wherein the fluoroalkane-containing hydrocarbon stream is comprised of at least 90 wt. % $C_3$ to $C_5$ hydrocarbons.

17. The process of claim 14, wherein the strong acid functionality is provided by sulfonic acid groups.

18. The process of claim 14, wherein the adsorbent is a strong cation exchange resin styrene/divinyl benzene copolymer resin having a sulfonic acid functionality.

19. The process of claim 14, wherein the fluoroalkanes are selected from the group consisting of 1-fluoropropane, 2-fluoropropane, 2-fluoro-2-methylpropane, 1-fluorobutane, 2-fluorobutane, 1-fluoro-2-methylbutane, 1-fluoropentane, 2-fluoropentane, 2,2-difluorobutane, 3-fluoropentane, 1,2-difluoropentane, 1-fluoro-3-methylbutane, and mixtures thereof.

* * * * *